(12) United States Patent
Heckele et al.

(10) Patent No.: US 6,723,125 B2
(45) Date of Patent: Apr. 20, 2004

(54) DEVICE FOR CONDITIONING A LIGAMENT TO BE IMPLANTED

(75) Inventors: Helmut Heckele, Knittlingen (DE); Eberhard Körner, Bretten (DE); Martin Seebach, Oberderdingen (DE); Jürgen Göbel, Östringen (DE)

(73) Assignee: Richard Wolf GmbH, Knittlingen (DE)

( * ) Notice: Subject to any disclaimer, the term of this patent is extended or adjusted under 35 U.S.C. 154(b) by 270 days.

(21) Appl. No.: 09/965,477

(22) Filed: Sep. 27, 2001

(65) Prior Publication Data

US 2002/0040240 A1 Apr. 4, 2002

(30) Foreign Application Priority Data

Sep. 28, 2000 (DE) .......................... 100 49 270

(51) Int. Cl.[7] .................................. A61F 2/08
(52) U.S. Cl. .................. 623/13.13; 623/13.11
(58) Field of Search .................. 623/13.13, 13.12, 623/13.14, 13.15, 13.19, 13.2, 14.11

(56) References Cited

U.S. PATENT DOCUMENTS

| 4,712,542 A | 12/1987 | Daniel et al. |
| 4,955,910 A | 9/1990 | Bolesky |
| 5,281,422 A | 1/1994 | Badylak et al. |
| 5,397,357 A * | 3/1995 | Schmieding et al. ......... 606/86 |
| 5,713,897 A | 2/1998 | Goble et al. |
| 6,001,106 A | 12/1999 | Ryan et al. |
| 6,517,578 B2 * | 2/2003 | Hein ....................... 623/13.13 |

FOREIGN PATENT DOCUMENTS

| DE | 41 12 205 A1 | 10/1992 |
| DE | 689 07 711 T2 | 2/1994 |
| EP | 0 379 789 B1 | 8/1990 |
| EP | 0 379 789 A1 | 8/1990 |
| FR | 2 699 396 A1 | 6/1994 |
| WO | WO 01/93771 A1 | 12/2001 |

* cited by examiner

Primary Examiner—Corrine McDermott
Assistant Examiner—Hieu Phan
(74) Attorney, Agent, or Firm—Akin Gump Strauss Hauer & Feld LLP

(57) ABSTRACT

The device for conditioning an organic ligament to be implanted, in particular a ligament as a cruciate ligament replacement, is equipped with first and second receiving elements for receiving and tensioning the ligament at two spaced locations. The first receiving elements is connected to means for the periodic translatory adjustment of the first receiving element with respect to the ligament.

8 Claims, 1 Drawing Sheet

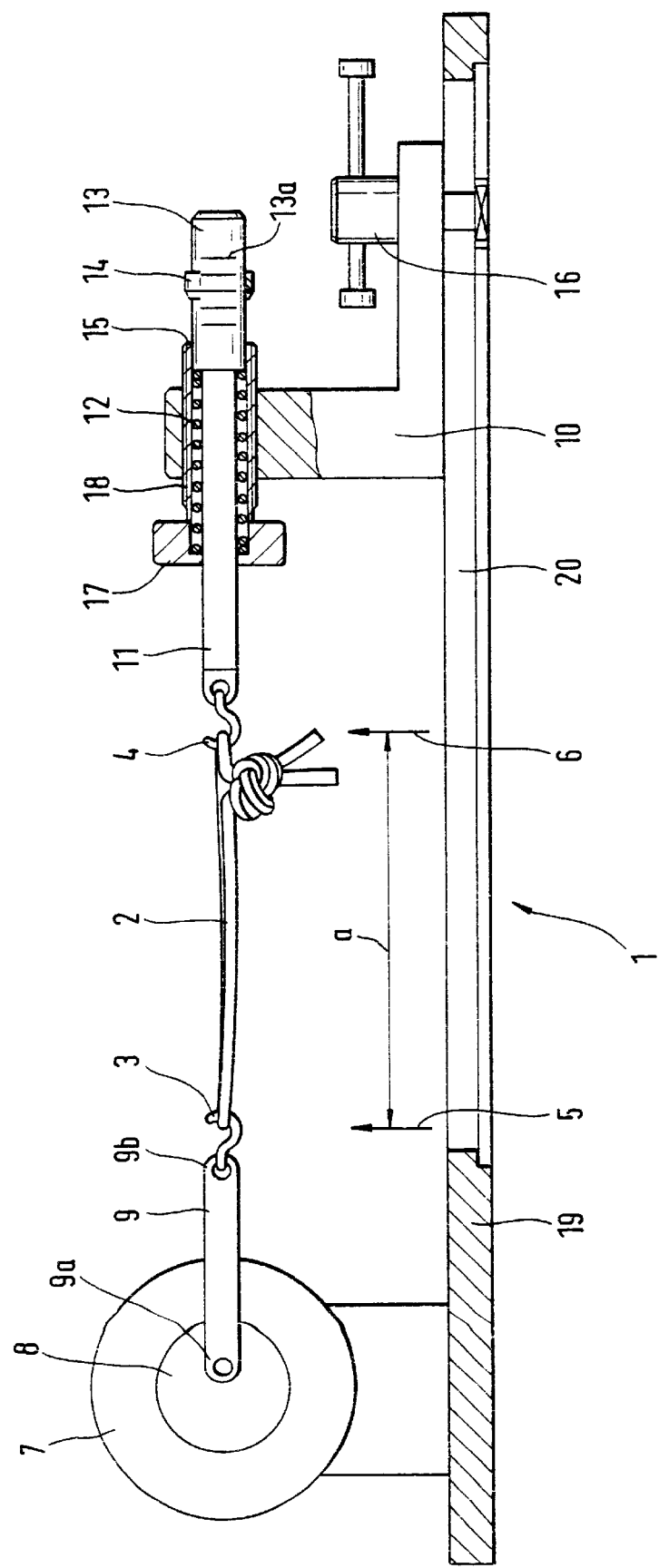

DEVICE FOR CONDITIONING A LIGAMENT TO BE IMPLANTED

BACKGROUND OF THE INVENTION

The invention relates to a device for conditioning an organic ligament to be implanted, in particular a ligament as a cruciate ligament replacement.

In cruciate ligament plasty as a rule organic ligaments from the body of the patient are applied. These ligaments with a re-loading after operation often experience a length change. This may lead to renewed instabilities of the knee joint. Therefore one strives to condition the ligament before implantation, i.e. the ligament is preoperatively stretched to a permanent length so that a later length change may not occur.

It is known that the ligament to be implanted is stretched by the operator directly before or during the operation by the application of force, wherein one assumes that the ligament loses the property of extending later. With this the ligament is, for example, tied together into a loop and received between both hands or index fingers and stretched.

With this there is the disadvantage that the manual stretching among other things depends individually on the condition of the operator, so that inasmuch as this is concerned there are to be expected no reproducible and exact stretching results, not least because these also depend on the nature of the respective ligament itself.

BRIEF SUMMARY OF THE INVENTION

It is therefore the object of the invention to provide a device with which it is possible to simulate the procedure of the manual stretching and to carry out a permanent extension of the ligament, which can be estimated in its extent, so that the intensity of the conditioning may also be carried out with differently stable ligaments in a reproducible manner.

For achieving this object the device for conditioning a ligament according to the invention comprises a first and a second receiving element for receiving and for tensioning the ligament at two spaced points, wherein the first receiving element is connected to means for the periodic, and with respect to the ligament, translatory adjustment of the first receiving element.

The strip is thus accommodated at the receiving elements in the device and subjected mechanically to a preferably adjustable periodic alternating load for so long until one finally may assume from experience values that the ligament is sufficiently stretched, and after the implantation, e.g. as a cruciate ligament replacement, is no longer extended.

The means for the periodic adjustment of the receiving element comprises a disk which is driven by a motor and onto which a crank is arranged eccentrically and linkingly with one of its ends. At the other end of the crank there is fastened the receiving element. With this conception there is thus effected the periodic stretching of the ligament with an eccentric drive.

The two receiving elements are usefully formed as a hook into which the ligament in the form of a loop may be loosely hung. The one hook which forms the second receiving element is arranged on a linearly displaceable unit. This unit comprises an axially displaceably mounted rod which is connected to an elastic element which is rigidly arranged on it and which may be a helical spring. With this it is the case of a compression spring which holds the ligament tensioned, wherein the rod in operation of the device is adjusted against or with the action of the spring according to the position of the eccentric.

For the reproducibility of the conditioning it is important that the force which the device exerts on the tensioned ligament be measured and where appropriate may also be adjusted. It is therefore further envisaged that the mentioned displaceable unit comprises means for measuring the maximum force exerted by the elastic element onto the rod. These force measuring means, in a simple embodiment, consist of a sliding ring placed on a cylindrical part as well as an abutment for the sliding ring.

Furthermore, for the purpose of adjustability to various length ligaments or ligament loops, the device comprises further adjusting means for adjusting the distance between the two receiving elements or hooks.

For an exact adjusting of the ligament loading the linearly displaceable unit has tensioning means for setting and fixing the axial position of the mentioned rod relative to this unit. A simple embodiment thereby results with the use of a screw and a nut as a tensioning means.

With the suggested device it is possible, in contrast to a conditioning by hand, to be able to achieve a reproducible and, according to demand, an exact and sufficient conditioning of the ligament. In particular, on account of the previous alternating loadings, it may be insured that the ligament has experienced its largest possible length change before the implantation so that damaging length changes on account of natural loading may be ruled out later after implantation.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings on embodiment which is presently preferred. It should be understood, however, that the invention is not limited to the precise arrangements and instrumentalities shown. In the drawings:

The sole FIGURE schematically shows a lateral view of a conditioning device according to the invention.

DETAILED DESCRIPTION OF THE INVENTION

The device 1 is assembled on a base plate 19 on which a motor is stationarily arranged which drives a vertically mounted disk 8. On this disk there is linkingly arranged a crank 9 with its one end 9a. The other end 9b of the crank is connected to an open hook 3 which represents the first receiving element for the ligament 2 to be conditioned.

According to the representation the, ligament is tied into a loop and knotted at the ends. The one end of the loop is hung in the hook 3, while the other loop end is carried or accommodated by a hook 4 as a second receiving element. The two hooks 3 and 4 are located at two points or locations 5 and 6 at a distance "a" to one another.

The hook 4 is arranged on a fixable unit 10 linearly displaceable on the base plate 19. This unit and thus also the hook 4 are displaceable relative to the motor 7. A T-groove guide 20 thereby permits the guiding and fixing of the unit 10 on the base plate 19 with adjusting and fixing means 16, wherein the unit 10 is fastened on the base plate 19 when it is located at its required distance to the motor 7, thus when the two hooks 3 and 4 have the required distance "a" to one another, this distance depending on the length of the ligament loop.

The unit 10 comprises a nut 18 in which a screw 17 is screwed. The screw 17 and the nut 18 represent tensioning means with which an axially displaceably mounted rod 11 may be adjusted with respect to its axial position relative to unit 10. The rod 11 carries the second hook 4. A helical spring 12 acts between the unit 10 and the rod 11 such that the rod 11 via the spring 12 is elastically mounted with respect to the unit 10.

The rod 11 comprises a cylindrical part 13 on which a sliding ring 14 is pushed. An abutment 15 on the screw 17 ensures that the sliding ring 14 may only reach up to a certain position with an axial displacement of the rod 11 on the cylindrical part 13. At a scale 13a, calibrated with respect to the spring force, on the cylindrical part 13 then at the position of the sliding ring 14 the force of the spring 12 which is maximally exerted onto the hook 4 and thus onto the ligament 2 may be measured or read off.

The conditioning of the ligament 2 is effected such that it first is formed into a loop and is knotted at the ends and then with the loop ends is hung into the two hooks 3 and 4. Via the adjusting means 16 the unit 19 is moved to the position at which the hooks have a distance "a" which the hooks have to one another between the two hook positions 5 and 6 and at which the ligament is not tensioned or only a little. Thereafter the unit 10 with the help of the adjusting means 16 is fastened on the base plate 19.

In operation of the motor 7 via the then rotating disk 8 and the crank 9 there arises a periodic and essentially translatory adjusting of the hook 3 relative to the unit 10. By rotating the tensioning screw 17 the intensity and the maximum of the forces acting on the ligament 2 may be set. As has already been mentioned, from the scale 13a one may read off how large the alternating load acting on the ligament 2 is, wherein of course there also exists the possibility of changing the maximum of the force, according to requirement, in the previously described manner by rotating the tensioning screw 17 in the one or the other direction in the context of a fine adjustment.

By way of the dynamic load the ligament 2 is periodically alternately loaded and stretched, wherein by way of the selection of the treatment time and the intensity of the load change one may assume an influence on the result of the conditioning. This time and the intensity are professionally selected according to experience values such that the ligament 2 after the conditioning procedure is maximally stretched without damage so that one may assume that no further length change is given after the implantation.

Otherwise, the device according to the invention may be set by way of a suitable positioning of the unit 10 relative to the motor 7 and adjusting of the tensioning screw 17 relative to the unit 10, such that the ligament 2 to be stretched is periodically stretched with a force which lies between zero and a selected maximal value, by which means there results a particularly efficient conditioning.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A device for conditioning an organic ligament to be implanted, in particular a ligament as a cruciate ligament replacement, comprising a first and a second receiving element for receiving and tensioning the ligament at two spaced locations, wherein the first receiving element is connected to means for the periodic translatory adjustment of the first receiving element with respect to the ligament, and wherein the means for adjusting the first receiving element comprises a disk which is driven by a motor and onto which there is arranged eccentrically and linkingly a crank with one of its ends, and the first receiving element is arranged at the other end of the crank.

2. The device according to claim 1, wherein the two receiving elements are each designed as a hook.

3. A device for conditioning an organic ligament to be implanted, in particular a ligament as a cruciate ligament replacement, comprising a first and a second receiving element for receiving and tensioning the ligament at two spaced locations, wherein the first receiving element is connected to means for the periodic translatory adjustment of the first receiving element with respect to the ligament, wherein the second receiving element is arranged on a linearly displaceable and fixable unit, and wherein the unit comprises an axially displaceably mounted rod which carries the second receiving element and is connected to an elastic element rigidly arranged on it.

4. The device according to claim 3, wherein the elastic element is a helical spring against whose action the rod is displaceable.

5. The device according to claim 3, wherein the unit comprises means for measuring the maximum force exerted via the elastic element onto the rods.

6. The device according to claim 5, wherein the means for measuring the force comprises a sliding ring placed onto the cylindrical part of the rod as well as an abutment for the sliding ring.

7. The device according to claim 3, wherein the unit is provided with adjusting means for adjusting the distance between the two receiving elements.

8. The device according to claim 3, wherein the unit comprises tensioning means for setting the axial position of the rod relative to it.

* * * * *